United States Patent
Clerc et al.

(10) Patent No.: US 8,016,749 B2
(45) Date of Patent: Sep. 13, 2011

(54) VISION CATHETER HAVING ELECTROMECHANICAL NAVIGATION

(75) Inventors: Claude O Clerc, Marlborough, MA (US); John Hutchins, North Attleboro, MA (US); Alexandra Rousseau, Cambridge, MA (US); F Anthony Headley, Jr., Marlborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1112 days.

(21) Appl. No.: 11/385,320

(22) Filed: Mar. 21, 2006

(65) Prior Publication Data

US 2007/0225559 A1 Sep. 27, 2007

(51) Int. Cl.
*A61B 1/00* (2006.01)
*A61B 1/012* (2006.01)

(52) U.S. Cl. ......... 600/117; 600/128; 600/153; 600/156

(58) Field of Classification Search .................. 600/103, 600/113, 117, 128, 424, 153, 156; 604/523
See application file for complete search history.

(56) References Cited

U.S. PATENT DOCUMENTS

| | | | |
|---|---|---|---|
| 4,586,491 A | 5/1986 | Carpenter | |
| 4,616,631 A * | 10/1986 | Takahashi | 600/139 |
| 4,759,348 A * | 7/1988 | Cawood | 600/102 |
| 5,042,486 A * | 8/1991 | Pfeiler et al. | 600/424 |
| 5,395,335 A * | 3/1995 | Jang | 604/102.02 |
| 5,727,553 A * | 3/1998 | Saad | 600/407 |
| 5,769,814 A * | 6/1998 | Wijay | 604/103.1 |
| 5,830,196 A * | 11/1998 | Hicks | 604/523 |
| 5,833,608 A * | 11/1998 | Acker | 600/409 |
| 5,840,024 A * | 11/1998 | Taniguchi et al. | 600/424 |
| 5,957,833 A * | 9/1999 | Shan | 600/117 |
| 6,036,654 A * | 3/2000 | Quinn et al. | 600/526 |
| 6,078,876 A | 6/2000 | Rosenberg et al. | |
| 6,125,337 A | 9/2000 | Rosenberg et al. | |
| 6,129,667 A * | 10/2000 | Dumoulin et al. | 600/424 |
| 6,135,946 A | 10/2000 | Konen et al. | |
| 6,188,355 B1 | 2/2001 | Gilboa | |
| 6,203,493 B1 | 3/2001 | Ben-Haim | |
| 6,211,666 B1 * | 4/2001 | Acker | 324/207.17 |
| 6,233,476 B1 * | 5/2001 | Strommer et al. | 600/424 |
| 6,295,368 B1 | 9/2001 | Hasegawa et al. | |

(Continued)

FOREIGN PATENT DOCUMENTS

WO WO03086492 A2 10/2003

(Continued)

OTHER PUBLICATIONS

Sheski, F.D., and P.N. Mathur, "Endoscopic Treatment of Early-Stage Lung Cancer," *Cancer Control* 7(1):35-44, Jan./Feb. 2000.

(Continued)

*Primary Examiner* — John P Leubecker
(74) *Attorney, Agent, or Firm* — Finnegan, Henderson, Farabow, Garrett & Dunner LLP (57) ABSTRACT

Embodiments of the present invention are generally directed to a visualization system including a small gauge vision catheter that is designed to be standalone or received within an instrument channel of a larger endoscope. The vision catheter has imaging means disposable within an imaging channel, a working channel, and an electromagnetic sensor element insertable into the working channel of the catheter to provide position tracking. The working channel of the catheter also provides access for therapeutic and diagnostic tools.

18 Claims, 5 Drawing Sheets

U.S. PATENT DOCUMENTS

| | | |
|---|---|---|
| 6,366,799 B1 | 4/2002 | Acker et al. |
| 6,453,190 B1 | 9/2002 | Acker et al. |
| 6,471,639 B2 * | 10/2002 | Rudischhauser et al. ..... 600/128 |
| 6,585,642 B2 * | 7/2003 | Christopher .................. 600/156 |
| 6,656,110 B1 | 12/2003 | Irion et al. |
| 6,690,963 B2 | 2/2004 | Ben-Haim et al. |
| 6,768,496 B2 | 7/2004 | Bieger et al. |
| 6,832,985 B2 | 12/2004 | Irion et al. |
| 6,850,794 B2 | 2/2005 | Shahidi |
| 6,871,086 B2 | 3/2005 | Nevo et al. |
| 6,890,297 B2 | 5/2005 | Belson |
| 6,892,090 B2 | 5/2005 | Verard et al. |
| 6,895,268 B1 | 5/2005 | Rahn et al. |
| 6,930,706 B2 | 8/2005 | Kobayashi et al. |
| 6,934,575 B2 | 8/2005 | Ferre et al. |
| 6,947,788 B2 | 9/2005 | Gilboa et al. |
| 6,980,921 B2 | 12/2005 | Anderson et al. |
| 6,992,477 B2 | 1/2006 | Govari |
| 7,020,512 B2 | 3/2006 | Ritter et al. |
| 7,052,455 B2 | 5/2006 | Hale et al. |
| 7,301,332 B2 * | 11/2007 | Govari et al. ............ 324/207.21 |
| 2002/0049375 A1 | 4/2002 | Strommer et al. |
| 2002/0052546 A1 | 5/2002 | Frantz et al. |
| 2002/0193662 A1 | 12/2002 | Belson |
| 2004/0034311 A1 | 2/2004 | Mihalcik |
| 2004/0097804 A1 | 5/2004 | Sobe |
| 2005/0075538 A1 | 4/2005 | Banik et al. |
| 2005/0182295 A1 | 8/2005 | Soper |
| 2005/0197536 A1 | 9/2005 | Banik et al. |
| 2005/0272971 A1 | 12/2005 | Ohnishi et al. |
| 2005/0272975 A1 | 12/2005 | McWeeney et al. |
| 2005/0283067 A1 | 12/2005 | Sobe |
| 2006/0015011 A1 | 1/2006 | Hasegawa et al. |
| 2006/0030753 A1 | 2/2006 | Boutillette et al. |
| 2006/0069451 A1 | 3/2006 | Sunaoshi |
| 2006/0074289 A1 | 4/2006 | Adler et al. |
| 2007/0106113 A1 * | 5/2007 | Ravo ............................ 600/113 |
| 2007/0161853 A1 * | 7/2007 | Yagi et al. ..................... 600/109 |
| 2007/0173693 A1 * | 7/2007 | Refael ........................... 600/144 |
| 2010/0198009 A1 | 8/2010 | Farr et al. |

FOREIGN PATENT DOCUMENTS

| | | |
|---|---|---|
| WO | WO 2005/023082 | 3/2005 |
| WO | WO2005094665 A2 | 10/2005 |
| WO | WO2005122884 A2 | 12/2005 |

OTHER PUBLICATIONS

*Steerable Catheter System*, Microvasive, 2-page product brochure, as early as 1988.

*Visicath Diagnostic and Therapeutic Airway Management*, Microvasive, 4-page product brochure, as early as 1988.

*Visicath Fiberoptic Devices*, Microvasive, 6-page price list, Jan. 1, 1988.

* cited by examiner

VISION CATHETER HAVING ELECTROMECHANICAL NAVIGATION

FIELD OF THE INVENTION

The present invention relates to medical devices, and in particular to imaging catheters.

BACKGROUND OF THE INVENTION

An endoscope is a piece of surgical equipment that has imaging capabilities so as to be able to provide images of an internal body cavity of a patient. Most minimally invasive surgical procedures performed in the gastrointestinal (GI) tract or other internal body cavities are accomplished with the aid of an endoscope. An endoscope typically includes one or more instrument channels through which other medical catheters/instruments can pass.

Typically, an endoscope is used to reach an area of interest within a body cavity and, thereafter, another instrument such as a surgical catheter is extended through the instrument channel of the endoscope to perform some desired procedure. In a pulmonary endoscopic procedure, one of the key characteristics of the endoscope is its outer diameter with respect to the bronchial tree through which it must pass. For example, a conventional bronchoscope is typically a two or three lumen structure that includes fiber optic bundles for imaging and illumination and an instrument channel for the application of suction and/or the placement of tools. A conventional bronchoscope typically has an instrument channel lumen with an internal diameter of about 2.0 mm to 2.8 mm, and an outer shaft diameter of approximately 5 or 6 millimeters. Such an endoscope is too large to navigate the bronchial branches of the periphery of the lung, which are typically in the range of 2 to 3 millimeters wide. As a consequence, a conventional bronchoscope can only reach about the third or fourth bifurcation level of the bronchial tree. If a tissue biopsy is needed at the periphery of the tree where it is too narrow for the bronchoscope to access, the biopsy forceps are often pushed blindly into the region of the tissue and the sample is obtained in the absence of visualization.

Another factor that complicates endoscopic exploration of the periphery of the lung is the complexity and number of bronchial branches that exist. Electromagnetic navigation systems have been developed by companies such as Super-Dimension® (Minneapolis, Minn.) and Mediguide® (Arlington, Va.) that allow for guided access to peripheral sites in the airways. The current navigation systems are limited, however, by the lack of means for directly visualizing the patient's anatomy at the distal location of the extended working channel. This lack of direct visualization may result in inaccurate initial targeting of a therapeutic site, such as a biopsy site, without any indication of whether the correct target tissue has been reached, due in part to tolerance issues on how accurate these systems can be. Also, a subsequent event such as patient movement or coughing may modify the target site after the sensor is removed from the working channel.

Therefore, to improve access to remote locations in the body there is a need for a small diameter visualization catheter with a working channel that can be used in conjunction with electromagnetic tracking.

SUMMARY OF THE INVENTION

To address these and other concerns, the present invention is a visualization system including a small gauge vision catheter having an imaging channel for imaging means and a separate working channel. An electromagnetic sensor element is included in the vision catheter to provide position tracking. In one embodiment, the position sensor is removably positioned in the working channel. The working channel also provides access for therapeutic and diagnostic tools. In some embodiments, the vision catheter may have a shaft with a maximum outer diameter of less than about 3.0 mm and is capable of insertion through an instrument channel of a bronchoscope. In other embodiments, the vision catheter may have a shaft with a maximum outer diameter of about 4.2 mm that includes an outer layer with a braided structure that may be directly inserted into a living body.

In another embodiment, the present invention provides a method of examining a patient. The method includes advancing an endoscope into a passageway of a patient and inserting a vision catheter into an instrument channel of the endoscope. The vision catheter includes an imaging channel and a separate working channel. A position sensor is inserted into the working channel of the vision catheter and an imaging mechanism is inserted into the imaging channel. The vision catheter is advanced beyond the distal end of the endoscope and image information and position tracking information are simultaneously transmitted from the distal end to the proximal end of the vision catheter.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

In traditional pulmonary endoscope systems, such as bronchoscopes, electromagnetic sensors have been developed that allow the guided delivery of catheters (often referred to as extended working channels) to target locations in the bronchi and peripheral airways of a patient. In operation, an electromagnetic sensor is fed through a single lumen of a catheter. The location of the sensor element is mapped, and the sensor element is removed from the lumen. An instrument is then inserted into the lumen for therapeutic intervention. However, as discussed above, the extended working channel/sensor systems do not provide direct imaging capability.

To address these and other problems, the present invention is a visualization system that includes a small gauge vision catheter with a working channel lumen and imaging channel that allows for simultaneous direct visualization and electromagnetic sensor tracking. In some embodiments, the vision catheter is adapted to be inserted through an instrument channel of an endoscope, such as a bronchoscope. In other embodiments, the vision catheter comprises an outer sheath and is adapted to function as a stand alone medical device.

The vision catheter and visualization system provides several advantages over the conventional extended working channel/sensor tracking systems mentioned above. For example, the present invention enables a physician to directly visualize the distal bronchi and also obtain a three-dimensional position with a sensor element in order to precisely orient the working channel for therapeutic intervention, such as for taking a biopsy sample. The present invention also minimizes the consequences of patient movement by allowing the physician to verify that the vision catheter is in a proper orientation if the tracking sensor has been removed, thereby allowing a higher yield during trans-bronchial biopsy procedures. The present invention also provides for better management and faster response to potential complications such as bleeding during a pulmonary procedure. The various embodiments of the vision catheter described herein may be used with both reusable and low cost, disposable endoscopes, such as an endoscope that is sufficiently inexpensive to manufacture such that it can be a single-use device as described in U.S. patent application Ser. Nos. 10/811,781, filed Mar. 29, 2004, now U.S. Pat. No. 7,413,543, and Ser. No. 10/956,007, filed Sep. 30, 2004, now U.S. Pat. No. 7,578,786, each of which are commonly assigned to Scimed Life Systems, Inc., now Boston Scientific Scimed, Inc. and are hereby incorporated by reference. The various embodiments of the vision catheter described herein may also be used with in vivo visualization systems as described in U.S. Patent Application Ser. Nos. 60/555,356, filed Mar. 23, 2004, 10/914,411 filed Aug. 9, 2004, 60/656,801, filed Feb. 25, 2005, PCT/US2005/009533, filed Mar. 23, 2005, and U.S. patent application Ser. No. 11/089,520, filed Mar. 23, 2005, each of which are commonly assigned to Scimed Life Systems, Inc., now Boston Scientific Scimed, Inc. and are hereby incorporated by reference.

Figure 1:
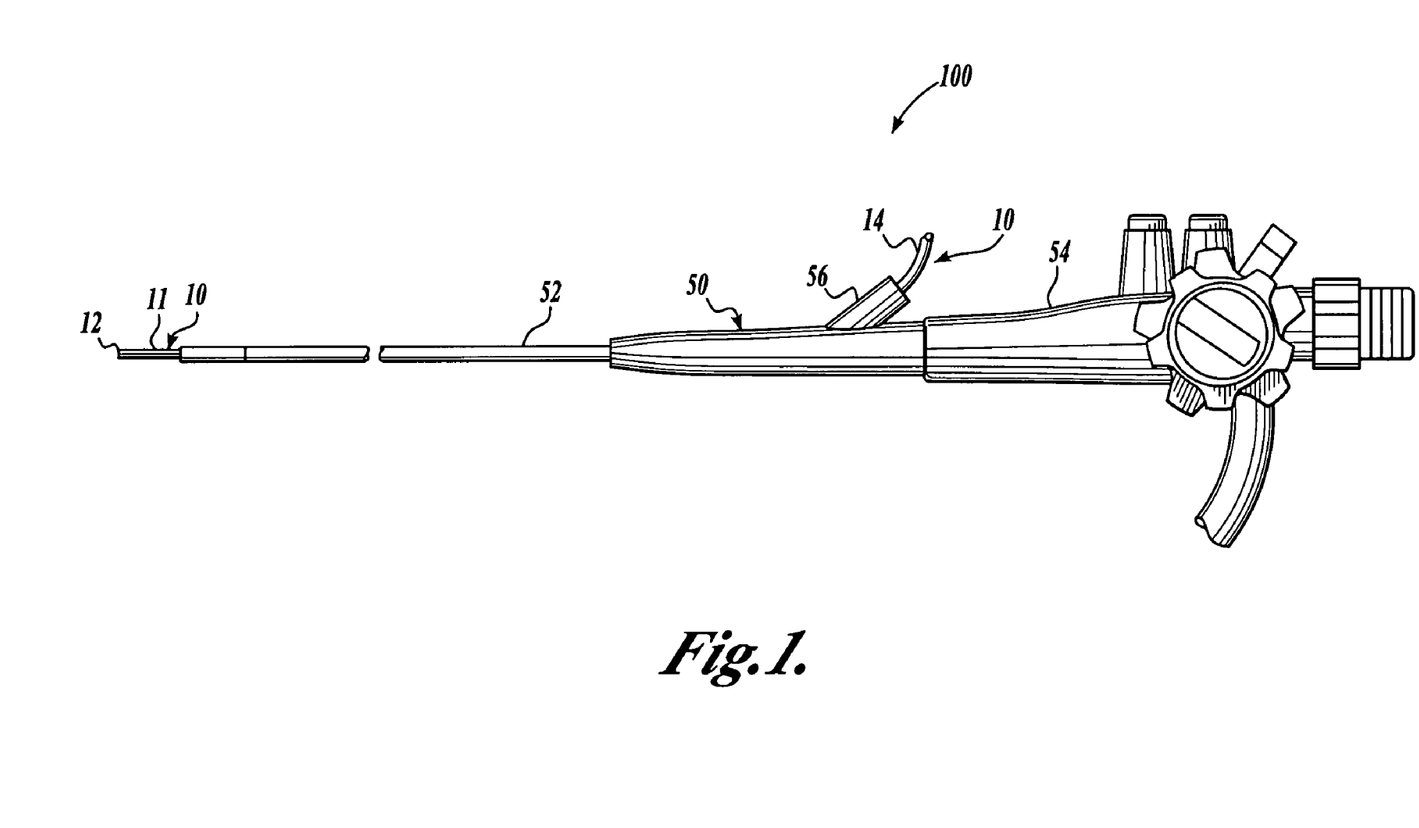
FIG. 1 is a schematic view of one embodiment of a visualization system comprising a vision catheter inserted into an instrument channel of a bronchoscope.

FIG. 1 is a simplified diagram of an embodiment of a visualization system 100 of the present invention. The visualization system 100 includes a small gauge vision catheter 10 having an elongated shaft 11 with a distal tip 12 for insertion into the body and a proximal end 14. The system 100 also includes a bronchoscope 50 having a flexible member 52 for insertion into the body and a handle 54 near the proximal end. The handle 54 is removably attached to a control unit (not shown) having an image processing system therein and a display monitor (not shown). As shown in FIG. 1, the vision catheter 10 may be inserted into a port 56 on the handle 54 and extended through an instrument channel lumen in the bronchoscope 50 such that the distal end 12 of the vision catheter 10 extends beyond the distal end of the flexible member 52 to form an extended working channel. As will be described in more detail below, contained within the shaft 11 of the vision catheter 10 is a working channel and an imaging channel for visualization of the examination scene surrounding the distal end 12 of the vision catheter.

Figure 2A:
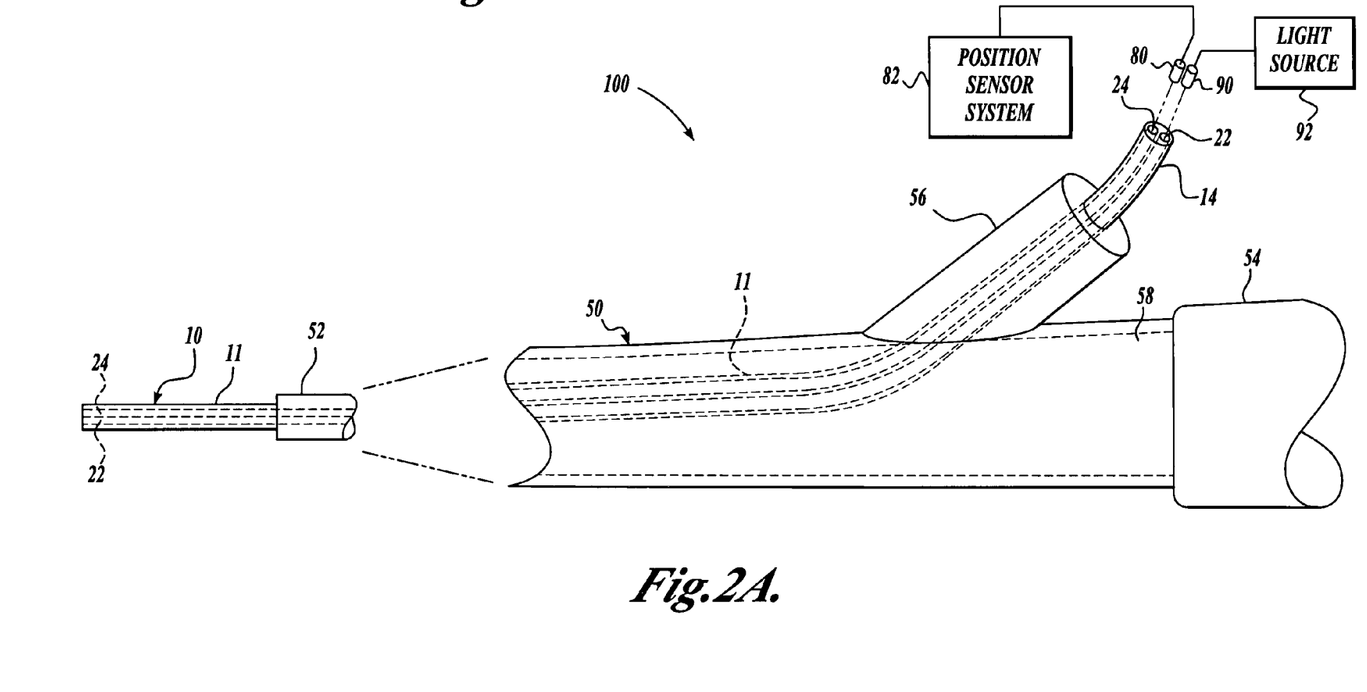
FIG. 2A is a schematic view illustrating the interconnection between the vision catheter and the bronchoscope shown in FIG. 1, in accordance with an embodiment of the present invention.

FIG. 2A is a partial cut-away view illustrating further detail of the connection between the vision catheter 10 and the bronchoscope 50, in accordance with one embodiment of the system 100 of the present invention. As shown in FIG. 2A, the shaft 11 of the vision catheter 10 includes an imaging channel 22 and a working channel 24 that each extend longitudinally between the proximal end 14 and the distal end 12 of the shaft 11. An instrument channel 58 extends within the bronchoscope to the distal end of the bronchoscope 50. The bronchoscope handle 54 includes the port 56 that forms an entrance into the instrument channel 58. As further shown in FIG. 2A, the distal end 12 of the vision catheter 10 is inserted through the port 56 and into the bronchoscope instrument channel 58 and protrudes from the distal end 52 of the bronchoscope 50.

Figure 2B:
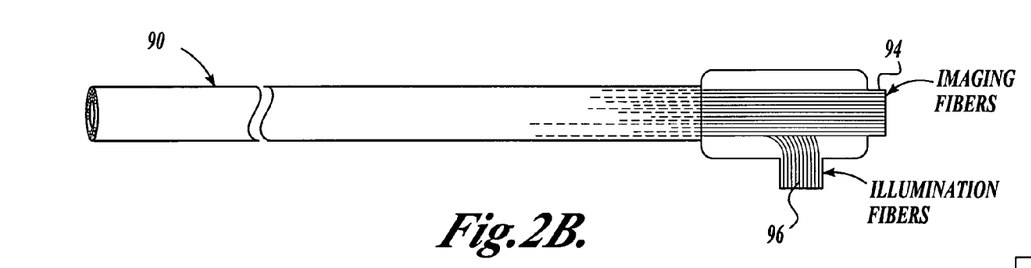
FIG. 2B is a schematic view of an embodiment of an imaging device for use with the vision catheter, in accordance with an embodiment of the present invention.

As mentioned previously, the vision catheter 10 includes the imaging channel 22 that serves as a conduit for an imaging device 90. In one embodiment the imaging device device 90 is an optical fiber bundle including one or more imaging fibers 94 and one or more illumination fibers 96, as shown in FIG. 2B. Preferably, the imaging device 90 includes one or more centrally extending coherent imaging fibers 94 and one or more circumferentially extending illumination fibers 96 that generally surround the one or more imaging fibers. A representative optical imaging device 90 is disclosed in commonly assigned U.S. patent application Ser. No. 10/914,411, filed Aug. 9, 2004, which is hereby incorporated by reference. Other examples of suitable optical imaging devices 90 for use in various embodiments of the invention are described in U.S. Patent Application Ser. Nos. 60/555,356, filed Mar. 23, 2004, 10/914,411, filed Aug. 9, 2004, 60/656,801, filed Feb. 25, 2005, PCT/US2005/009522, filed Mar. 23, 2005, and U.S. patent application Ser. No. 11/089,520, filed Mar. 23, 2005.

In operation, the imaging fibers 94 within the imaging device 90 transmit an image obtained at the distal end of the catheter 10 to a remote camera that displays the image on a monitor (not shown). As shown in FIG. 2A, the illumination fibers 96 within the imaging device 90 are coupled to the light source 92 so as to provide illumination at the distal end 12 of the shaft 11.

In some embodiments of the vision catheter 10, an objective lens or lenses (not shown) are placed at the distal end 12 of the shaft 11 in front of the imaging channel 22 to focus and/or amplify the image obtained with the imaging fibers. With regard to the field of view, focusing and magnification, the lens or lenses at the distal end of the imaging fiber may be made adjustable so as to increase the field of view and/or to allow for focus and additional magnification. The imaging channel 22 at the distal end 12 may be designed to have an additional lumen and/or port for flushing the lens so as to clean the surface, as described in more detail below.

The illumination source 92 for use in the system 100 may be of any suitable type of external light source such as a laser, halogen or mercury arc lamp source that supplies light to the imaging device 90 within the imaging channel 22 in order to illuminate an examination scene at the distal end 12 of the catheter 10. In some embodiments, the illumination source 92 is chosen for use with a particular therapeutic method. For example, the system 100 may be used in conjunction with autofluorescence technology to help diagnose lung cancer. The inability of conventional bronchoscopy to consistently detect early stage lung cancer has led to the development of the technique of fluorescence bronchoscopy for early detection of lung cancer. Fluorescence bronchoscopy is based on the fact that normal tissue fluoresces differently than abnormal tissue when exposed to an appropriate wavelength of light, and this difference can be detected. Xillix Technologies Corp., Lung Imaging Fluorescence Endoscope (LIFE) Vancouver, BC, illustrates this technology.

In another example, the system 100 may be used for pulmonary phototherapy. Phototherapy generally involves the preferential retention of a photosensitizer such as Photofrin® (porfimer sodium) by malignant or premalignant tissue, followed by the application of light with the imaging device inserted in the catheter to excite the sensitizer such that it interacts with oxygen to generate cytotoxins that destroy the abnormal tissue. The light exposure may be provided by a quartz fiber inserted through the working channel 24 or imaging channel 22 of the catheter 10 that illuminates the airway with a red laser light (630 nm). A cylindrical diffuser may be included at the tip of the quartz fiber to emit light over a broader pattern within the surrounding tissue.

As described above, the working channel 24 is disposed in the shaft 11 of the catheter 10 and is a conduit for receiving a position sensor element 80, and for receiving tools to take biopsies, applying medication, applying a vacuum, insufflation or irrigation, including a lens washing solution, as described in more detail below. The position sensor element 80 is preferably part of a position measuring system 82 that measures the position of the sensor element 80 within the vision catheter 10 relative to a three-dimensional frame of reference. The position sensor element 80 may be any suitable tracking device, such as, for example, a device with a magnetically responsive/active section that provides position and orientation information about the catheter 10. In one embodiment of the system 100, the position sensor 80 is part of a six degrees-of-freedom position measuring system 82 that detects the position and attitude of the catheter distal end 12 in three translational and three rotational degrees-of-freedom. The position sensor element 80 is capable of insertion into the working channel 24 of the vision catheter 10. One suitable tracking sensor element 80 and system is commercially available from SuperDimension, Inc., of Minneapolis, Minn. Such a position measuring system is a six degrees-of-freedom electromagnetic position measuring system and is described in U.S. Pat. No. 6,188,355, issued to Super Dimension Ltd., and incorporated herein by reference.

In operation of the system 100, a user (such as a bronchoscopist) inserts the bronchoscope 50 into the bronchial tree of a patient in a conventional fashion. When small bronchioli are reached that are too small in diameter to receive the bronchoscope 50, the user inserts the small gauge vision catheter 10 into the port 56 of the instrument channel 58 of the bronchoscope 50. The user then advances the vision catheter 10 beyond the distal end 52 of the bronchoscope 50. At the time of vision catheter 10 insertion, or at a later time, the user inserts the position sensor element 80 into the working channel 24; and inserts the imaging device 90 into the imaging channel 22 of the vision catheter 10. The progress of the catheter 10 into the bronchial tree is then observed via the tracking sensor system 82 and a real time view of the examination scene is captured from the imaging device 90 and directly visualized by the user on the display monitor 74 or through an eyepiece (not shown) attached to the imaging device 90. Once the distal end 12 of the catheter 10 is positioned in a desired location, the user records the position sensor information and may optionally superimpose position coordinates with other position information, such as fluoroscope information. The position sensor element 80 is then retracted from the working channel 24 of the vision catheter 10 in order to allow passage of therapeutic and/or diagnostic tools through the working channel 24. Throughout the positioning, diagnostic examination and/or therapeutic procedure, the user is able to monitor the examination scene through the use of the imaging device 90. Therefore, the system 100 provides a means for closely monitoring the position and orientation of the vision catheter 10, such that reintroduction of the position sensor 80 is not required to verify the catheter position after patient coughing or other patient movement.

In the system 100, the vision catheter 10 is a small gauge catheter having a lumen through which imaging means can be inserted, and a working channel. In some embodiments, the imaging device 90 is integrally formed with the vision catheter 10. In other embodiments, the imaging device 90 is removably inserted into the vision catheter 10. As described above, the vision catheter 10 is able to traverse tortuous airway passages to the peripheral airways in a manner as atraumatic to the patient as possible. Therefore, to limit insertion time and discomfort to the patient the vision catheter 10 is of the appropriate size and shape and is made of flexible materials that are responsive to maneuvering forces when guiding the vision catheter 10 into the desired position.

Figure 3A:
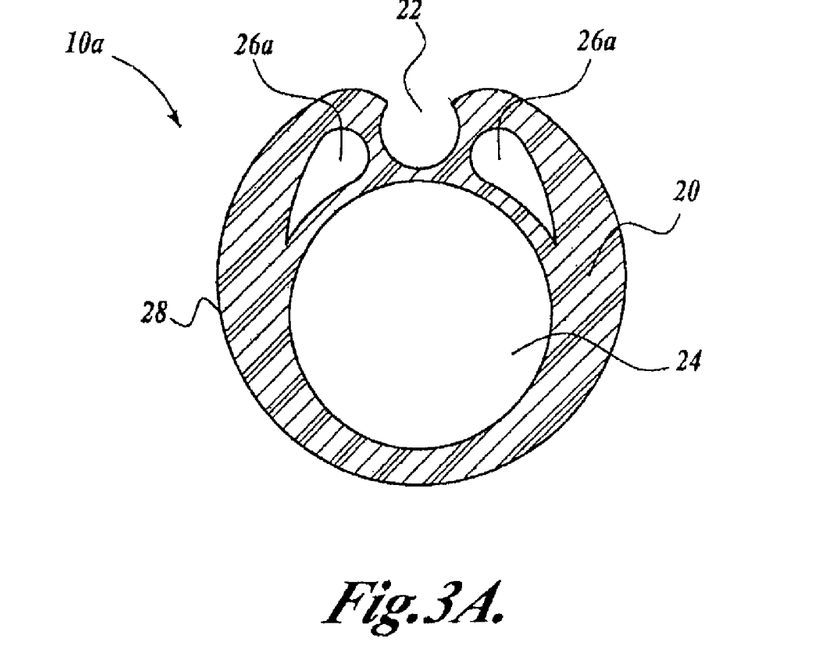
FIG. 3A is a cross-sectional view of an embodiment of the catheter shown in FIG. 1.

FIG. 3A shows a cross-sectional view of a shaft 28 of a vision catheter 10*a*, formed in accordance with an embodiment of the present invention. The shaft 28 of the catheter 10*a* includes an extruded shaft body 20 having an imaging channel 22 and a working channel 24 extending along a length thereof. As shown in FIG. 3A, in some embodiments of the vision catheter 10*a*, the imaging channel is a "C"-shaped, open lumen, whereby the circumference of the imaging channel 22 is not completely enclosed within the shaft body 20 in order to minimize the outer diameter of the shaft 28.

Additional channels 26*a* and 26*b* may be optionally included in the shaft body 20 to provide increased flexibility and/or functionality to the shaft 28. For example, the additional channels 26*a* and/or 26*b* shown in FIG. 3A may be used to provide fluids for flushing an objective lens at the distal tip of the shaft (not shown). In some embodiments, channels 26*a* and 26*b* extend from the proximal end to the distal end of the shaft 28. In alternative embodiments, channels 26*a* and 26*b* extend through only a portion of the shaft 28. As shown in FIG. 3A, in some embodiments of the catheter 10*a*, the channels 26*a* and 26*b* may be formed into a teardrop shape having a rounded first end adjacent the imaging channel 22 and a tapered second end adjacent the working channel 24. In some embodiments of the vision catheter 10*a*, the shaft 28 may have an outer diameter of approximately 2.7 mm to 3.0 mm to allow insertion into a bronchoscope having a working channel diameter of about 3.2 mm, such as, for example, the Pentax FB-19TV. In some embodiments, the imaging channel 22 may have a diameter of approximately 0.5 mm, and the working channel 24 may have a diameter of approximately 1.9 mm to 2.0 mm.

In one particular embodiment of the vision catheter 10*a*, the shaft body 20 is a four lumen extrusion having a C-shaped open imaging lumen. The shaft may have an outer diameter of less than 3.0 mm, such as 2.9 mm or less, such as 2.8 mm or less. In accordance with this embodiment, the working channel 24 may have a diameter of about 2.0 mm and the imaging channel 22 may have a diameter of about 0.5 mm.

Figure 3B:
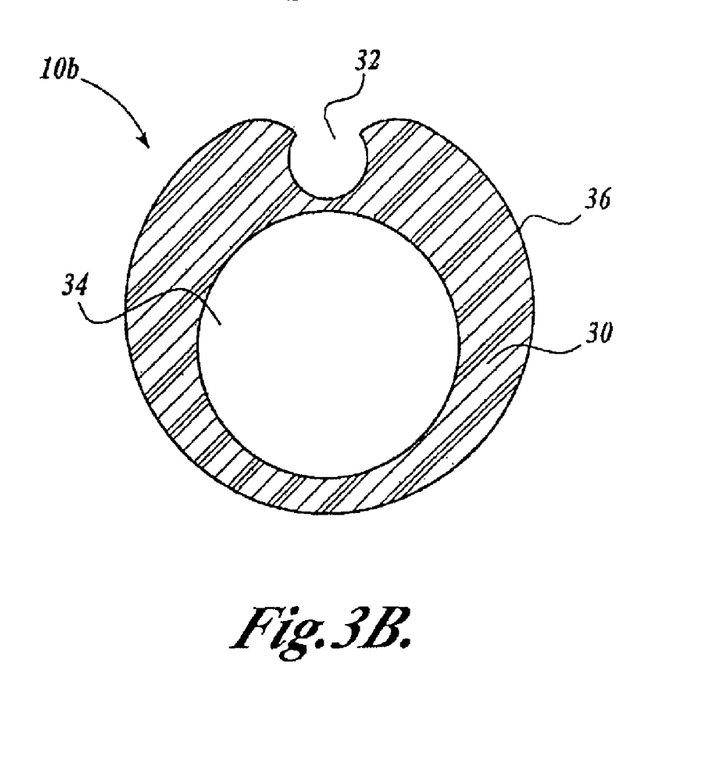
FIG. 3B is a cross-sectional view of another embodiment of the catheter shown in FIG. 1.

FIG. 3B shows a cross-section of a vision catheter shaft 36 in accordance with another embodiment of a vision catheter 10*b* of the present invention. The vision catheter shaft 36 has an extruded shaft body 30 that includes an imaging channel 32 and a working channel 34. In some embodiments of the catheter 10*b*, the shaft 36 may have an outer diameter of approximately 2.7 to 2.8 mm, the imaging channel 32 may have a diameter of approximately 0.5 mm and the working channel 34 may have a diameter of approximately 1.9 mm.

In one embodiment of the catheter 10b, the shaft body 30 is a two lumen extrusion having a C-shaped imaging lumen. The shaft may have an outer diameter of about 2.7 mm. In accordance with this embodiment, the working channel 34 may have a diameter of about 1.9 mm and the imaging channel may have a diameter of about 0.5 mm.

With reference to FIGS. 3A and 3B, the shaft bodies 20, 30 of the catheter shafts 28, 36 of the vision catheters 10a, 10b may be formed by extrusion or co-extrusion of a polymer(s). The shaft bodies 20, 30 may be constructed from any suitable biocompatible polymer material such as Pebax® (polyether block amides), nylon, polytetrafluoroethylene (PTFE), polyethylene, polyurethane, polypropylene, fluorinated ethylene propylene (FEP), thermoplastic elastomers, and the like, or combinations thereof. Extrusion technology can be used to provide any desired level of variable stiffness, torque or articulation that is desired. The shaft bodies 20, 30 may be formed of a single material using extrusion technique. In another embodiment, the shaft bodies 20, may be formed from multiple materials by joining multiple extruded sections by heat bonding, adhesive bonding, lamination or other known techniques. In some embodiments, polymers of various durometers are used, such that the distal end of the shaft bodies 20, 30 of the catheters 10a, 10b comprises a low durometer material and the proximal end of the shaft body of the catheters 10a, 10b comprise a high durometer material. In some embodiments, the shaft bodies 20, 30 are impregnated with a radiopaque material, such as barium sulfate or bismuth subcarbonate, to allow for partial visualization of the shaft 28, 36 during catheter procedures using fluoroscopic imaging. In some embodiments, as shown in FIG. 3A, the shaft body 20 may be extruded to contain additional voids and/or lumens, such as channels 26a and 26b to increase the flexibility of the shaft. In accordance with various embodiments of the invention, the vision catheter 10 may be made of low cost disposable materials such that it may be considered a single-use device.

In some embodiments, the shaft and/or distal tip of the catheter may be shaped or bent for access to specific pulmonary regions, such as a hockey stick type shape or other suitable shape for access into airway passages. The internal surface of the channels within the vision catheter may be lined or coated with a friction reducing material such as a lubricious polymer for ease of inserting the fiber optic bundle and position sensor, etc.

Figures 3C, 4, 5:
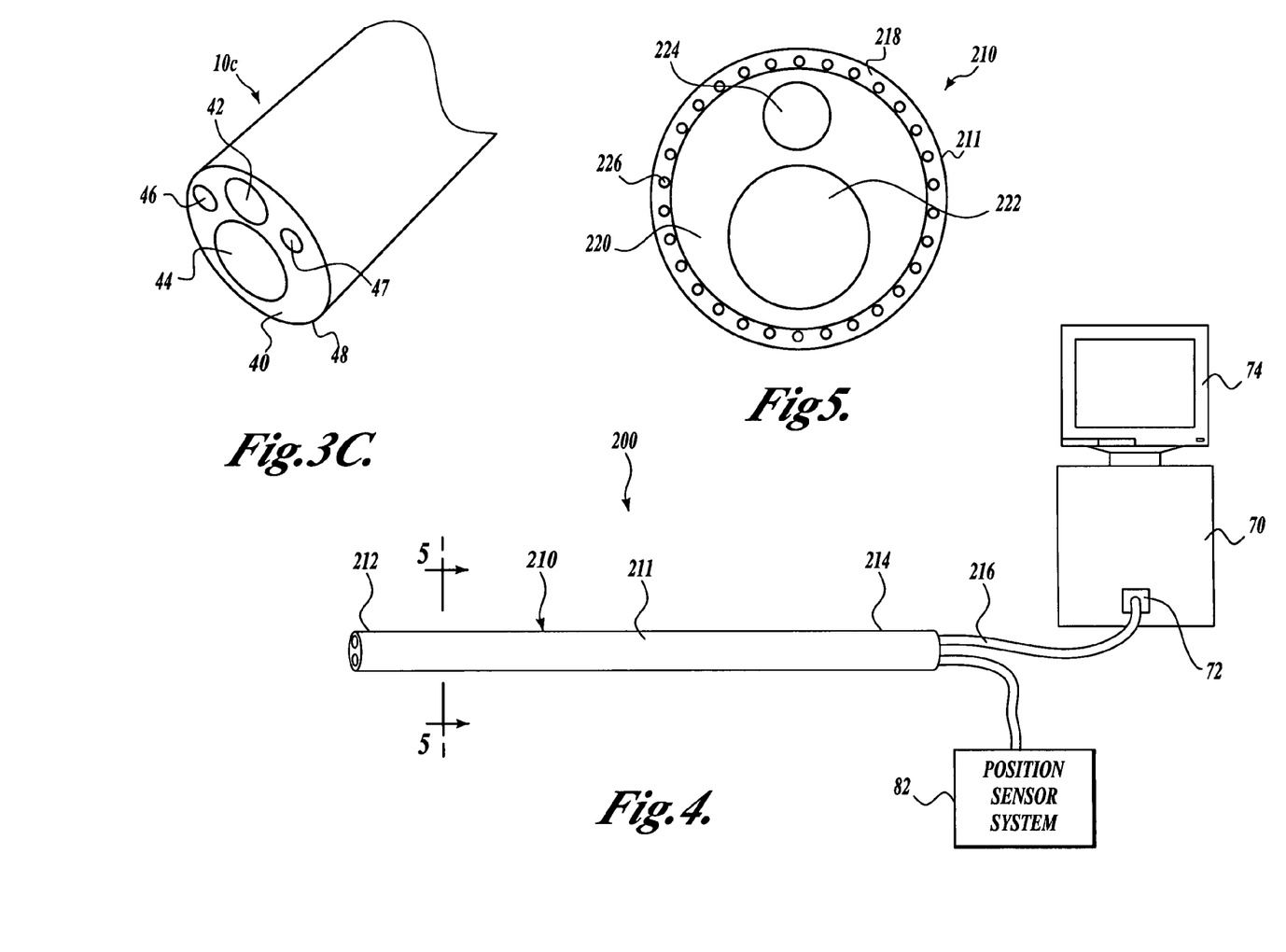
FIG. 3C is a cross-sectional view of yet another embodiment of the catheter shown in FIG. 1.
FIG. 4 is a schematic view of another embodiment of a visualization system comprising a vision catheter with a working channel and an imaging channel, a control unit and a display monitor in accordance with an embodiment of the present invention.
FIG. 5 is a cross-sectional view of an embodiment of the catheter shown in FIG. 4.

FIG. 3C shows a cross section of a shaft 48 of a vision catheter 10c, formed in accordance with yet another embodiment of the present invention. The distal end 48 of the shaft has a distal face 40 with a number of ports including a camera port 42, an entrance to a working channel 44, and illumination ports 46 and 47. In some embodiments, the imaging system may include a solid state sensor disposed at or adjacent the distal end of the vision catheter shaft 48. The solid state imaging system (not shown) is disposed behind the camera port 42, and an illumination assembly (not shown) is disposed behind illumination ports 46 and 47. The image sensor may be a CMOS image sensor or other solid state image sensor. The illumination source(s) are positioned in corresponding illumination ports 46 and 47 on the distal face 40 of the catheter 10c and generally comprise one or more light emitting diodes (LEDs) disposed on a substrate that are powered via wires that extend through a lumen to a power source at the proximal end of the catheter (not shown). The shaft body 40 may be formed as described above in reference to the catheters 10a and 10b. In some embodiments of the catheter 10c, the outer diameter of the shaft is approximately 2.7 to 2.8 mm.

FIG. 4 shows an alternative embodiment of a visualization system 200 having a small gauge vision catheter 210 that may be used as a stand alone device (i.e., without requiring the use of an endoscope or bronchoscope). The small gauge vision catheter 210 has an elongated shaft 211 with a distal tip 212 for insertion into the body and a proximal end 214 with attachment means for attaching to an automated steering system 70 or a manually controlled handle (not shown) that tension one or more pull wires within the catheter 210 to direct the distal tip in a desired direction. The vision catheter 210 includes a working channel, an imaging channel and an imaging channel, as described above in reference to the system 100, and additionally includes a reinforcement sheath for added maneuverability such that it may be used in the absence of an endoscope such as a bronchoscope, as described in more detail below.

FIG. 5 shows a cross-sectional view of the shaft 211 shown in FIG. 4. The shaft 211 has an extruded shaft body 220 having a working channel 222, an imaging channel 224, and a sheath 218 surrounding the shaft body 220. The shaft 211 may also include an inner reinforcement layer 226, for example, a metallic or polymeric braid, disposed between the shaft body 220 and the outer sheath 218 as shown in FIG. 5. The inner reinforcement layer 226 encases the length of the shaft body 220, or portions thereof to provide sufficient torque and kink resistance to the catheter 210 to allow for proper positioning within a pulmonary airway without routing it through an endoscope, such as a bronchoscope. In some embodiments, the catheter 210 may have an outer diameter in the range of approximately 4.0 mm to about 4.2 mm, with a working channel 222 that may have a diameter of approximately 1.9 mm to 2.1 mm, and an imaging channel 224 that may have a diameter of approximately 0.5 mm to about 0.9 mm.

In one embodiment of the catheter 210, the shaft 211 may have an outer diameter of 4.15 mm. In accordance with this embodiment, the shaft 211 comprises the double lumen extruded shaft body 220, the outer polymeric layer 218 and the inner reinforcement sheath 226 disposed therebetween. In accordance with this embodiment, the working channel may have a diameter of about 2.0 mm and the imaging channel may have a diameter of about 0.9 mm.

In operation of the system 200, the distal end of the catheter 210, including a position sensor element that is positioned in the working channel 222 and an imaging element that is positioned in the imaging channel 224, is advanced into a patient's airway until the desired location is reached. The location of the distal end 212 is tracked using the position sensor system 82. The position sensor element is then retracted from the working channel 222. The user may then insert therapeutic and/or diagnostic tools into the working channel 222.

Figure 6:
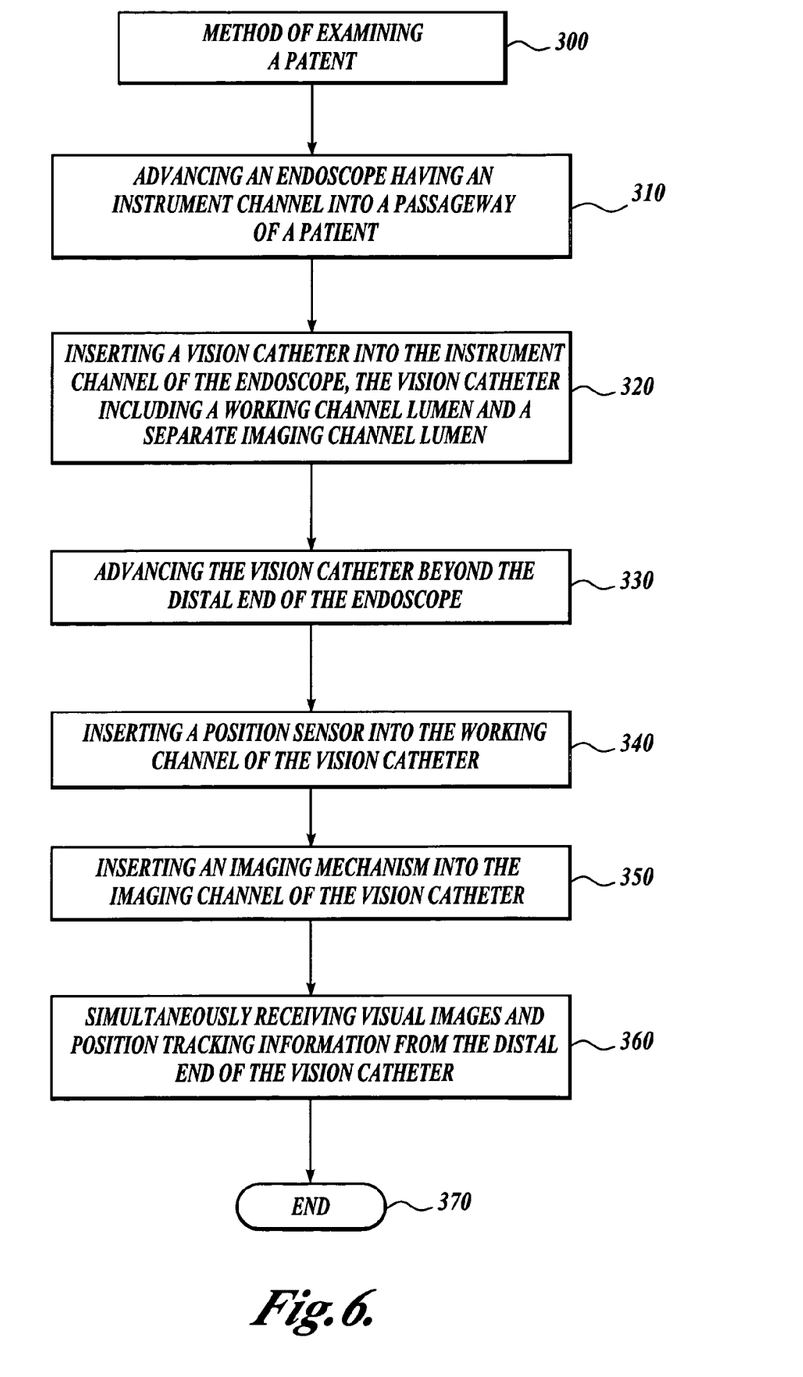
FIG. 6 is a flow diagram illustrating a method of using the vision catheter to examine a patient in accordance with another embodiment of the present invention.

In another embodiment, the present invention provides a method of examining a patient as shown in FIG. 6. The method starts at 300 and comprises advancing an endoscope having an instrument channel into a passageway of a patient at 310. At 320 the method further includes inserting a vision catheter into the instrument channel of the endoscope. The vision catheter includes a working channel lumen and a separate imaging channel lumen. The vision catheter is advanced to the distal end of the endoscope at 330. At 340 a position sensor is inserted into the working channel of the vision catheter. At 350 an imaging mechanism is inserted into the imaging channel of the vision catheter. At 360 the method includes simultaneously receiving visual images and position tracking information from the distal end of the vision catheter. Once position tracking information is obtained, the position sensor may be removed from the working channel and other tools and therapeutic devices may be inserted through the working channel.

While described in reference to pulmonary applications, the vision catheter and system may be used in any region of the body requiring manipulation through passages having a small diameter that require positional tracking, such as cardiology, etc.

While the preferred embodiment of the invention has been illustrated and described, it will be appreciated that various changes can be made therein without departing from the scope of the invention. It is therefore intended that the scope of the invention be determined from the following claims and equivalents thereof.

The embodiments of the invention in which an exclusive property or privilege is claimed are defined as follows:

1. A vision catheter, comprising:
   a shaft having a distal end, a proximal end and a number of lumens therein including a working channel lumen and a separate imaging channel lumen, the shaft having a diameter that allows it to be inserted into an instrument channel of an endoscope;
   a position sensor positioned at or adjacent the distal end of the shaft that aids in determining the position of the distal end in a patient; and
   an imaging mechanism positioned in the imaging channel lumen for obtaining images of the patient,
   wherein the position sensor and the imaging mechanism can be simultaneously present in the shaft,
   wherein the imaging channel lumen comprises a C-shaped lumen open to an external environment along a longitudinal portion of the imaging channel lumen;
   wherein the shaft includes an additional channel that has a tear-drop shape having a rounded portion and a tapered portion;
   wherein the rounded portion of the tear-drop shaped additional channel is positioned adjacent to the C-shaped lumen, and the tapered portion of the tear-drop shaped additional channel tapers away from the C-shaped lumen to a narrowest portion of the tear-drop shaped additional channel.

2. The vision catheter of claim 1, wherein the position sensor is removably positioned in the working channel lumen of the shaft.

3. The vision catheter of claim 1, wherein the imaging mechanism is removably positioned in the imaging channel lumen.

4. The vision catheter of claim 3, wherein the imaging mechanism is a fiber optic catheter including a coherent bundle of imaging fibers and a bundle of illumination fibers.

5. The vision catheter of claim 4, wherein imaging fibers capture an image representing the tissue surrounding the distal end of the shaft and the proximal end of the shaft outputs the sensed image signals to an image processing system.

6. The vision catheter of claim 1, wherein the shaft has a maximum outer diameter of about 3.0 mm.

7. The vision catheter of claim 6, wherein the imaging channel lumen has a maximum diameter of about 0.5 mm.

8. The vision catheter of claim 6, wherein the working channel lumen has a maximum diameter of about 2.0 mm.

9. The vision catheter of claim 1, wherein the shaft has a maximum outer diameter of about 2.7 mm.

10. The vision catheter of claim 9, wherein the imaging channel lumen has a maximum diameter of about 0.5 mm.

11. The vision catheter of claim 9, wherein the working channel lumen has a maximum diameter of about 1.9 mm.

12. The vision catheter of claim 1, wherein the tapered portion of the tear-drop shaped additional channel tapers to a point.

13. A method for examining a patient, comprising:
    advancing an endoscope into a passageway of the patient, the endoscope comprising an instrument channel;
    inserting a vision catheter into the instrument channel of the endoscope, the vision catheter comprising a shaft having a distal end, a proximal end and a number of lumens therein including a working channel lumen and a separate imaging channel lumen;
    inserting a position sensor into the working channel lumen of the vision catheter;
    inserting an imaging mechanism into the imaging channel lumen of the vision catheter;
    advancing the vision catheter beyond the distal end of the endoscope; and
    simultaneously receiving visual images and position tracking information from the distal end of the vision catheter,
    wherein the imaging channel lumen comprises a C-shaped lumen open to an external environment along a longitudinal portion of the imaging channel lumen;
    wherein the shaft includes an additional channel that has a tear-drop shape having a rounded portion and a tapered portion;
    wherein the rounded portion of the tear-drop shaped additional channel is positioned adjacent to the C-shaped lumen, and the tapered portion of the tear-drop shaped additional channel tapers away from the C-shaped lumen to a narrowest portion of the tear-drop shaped additional channel.

14. The method of claim 13, wherein the visual images are received from a fiber optic catheter including a coherent bundle of imaging fibers and a bundle of illumination fibers.

15. The method of claim 13, wherein the position tracking information is received from an electromagnetic sensor element.

16. The method of claim 13, further comprising removing the position sensor element and inserting a therapeutic instrument into the working channel lumen.

17. The method of claim 13, wherein the vision catheter is advanced into a peripheral airway of the patient.

18. The method of claim 13, wherein the tapered portion of the tear-drop shaped additional channel tapers to a point.

* * * * *

UNITED STATES PATENT AND TRADEMARK OFFICE
CERTIFICATE OF CORRECTION

| | | |
|---|---|---|
| PATENT NO. | : 8,016,749 B2 | Page 1 of 1 |
| APPLICATION NO. | : 11/385320 | |
| DATED | : September 13, 2011 | |
| INVENTOR(S) | : Clause O. Clerc et al. | |

It is certified that error appears in the above-identified patent and that said Letters Patent is hereby corrected as shown below:

Title page, item 75 (inventors), line 1, "Claude O Clerc" should read --Clause O. Clerc--

Title page, item 75 (inventors), line 4, "F Anthony Headley" should read --F. Anthony Headley--

Signed and Sealed this
Twenty-second Day of November, 2011

David J. Kappos
*Director of the United States Patent and Trademark Office*

UNITED STATES PATENT AND TRADEMARK OFFICE
CERTIFICATE OF CORRECTION

PATENT NO. : 8,016,749 B2  Page 1 of 1
APPLICATION NO. : 11/385320
DATED : September 13, 2011
INVENTOR(S) : Claude O. Clerc et al.

It is certified that error appears in the above-identified patent and that said Letters Patent is hereby corrected as shown below:

Title page, item 75 (inventors), line 1, "Claude O Clerc" should read --Claude O. Clerc--

Title page, item 75 (inventors), line 4, "F Anthony Headley" should read --F. Anthony Headley--

This certificate supersedes the Certificate of Correction issued November 22, 2011.

Signed and Sealed this
Fourth Day of September, 2012

David J. Kappos
*Director of the United States Patent and Trademark Office*